United States Patent
Kato et al.

(10) Patent No.: US 12,325,642 B2
(45) Date of Patent: Jun. 10, 2025

(54) POROUS ZIRCONIA PARTICLES, AND AGGREGATE FOR IMMOBILIZING PROTEIN

(71) Applicants: NGK Spark Plug Co., LTD., Nagoya (JP); NATIONAL INSTITUTE OF ADVANCED INDUSTRIAL SCIENCE AND TECHNOLOGY, Tokyo (JP)

(72) Inventors: Katsuya Kato, Nagoya (JP); Fukue Nagata, Nagoya (JP); Shinjiro Kasahara, Nagoya (JP); Jun Otsuka, Nagoya (JP); Yuki Hirobe, Nagoya (JP)

(73) Assignees: NITERRA CO., LTD., Nagoya (JP); NATIONAL INSTITUTE OF ADVANCED INDUSTRIAL SCIENCE AND TECHNOLOGY, Tokyo (JP)

(*) Notice: Subject to any disclaimer, the term of this patent is extended or adjusted under 35 U.S.C. 154(b) by 994 days.

(21) Appl. No.: 17/424,640

(22) PCT Filed: Jan. 17, 2020

(86) PCT No.: PCT/JP2020/001498
§ 371 (c)(1),
(2) Date: Jul. 21, 2021

(87) PCT Pub. No.: WO2020/153253
PCT Pub. Date: Jul. 30, 2020

(65) Prior Publication Data
US 2022/0089453 A1 Mar. 24, 2022

(30) Foreign Application Priority Data
Jan. 24, 2019 (JP) ................................. 2019-010342

(51) Int. Cl.
*B01J 20/02* (2006.01)
*B01J 20/06* (2006.01)
(Continued)

(52) U.S. Cl.
CPC .............. *C01G 25/02* (2013.01); *B01J 20/06* (2013.01); *B01J 20/28016* (2013.01);
(Continued)

(58) Field of Classification Search
CPC ... C01P 2006/14; C01P 2006/17; B01J 20/06; B01J 20/28016; B01J 20/28069;
(Continued)

(56) References Cited

U.S. PATENT DOCUMENTS 5,015,373 A   5/1991   Carr et al.
5,141,634 A   8/1992   Carr et al.
(Continued)

FOREIGN PATENT DOCUMENTS

EP   2093195 A1   8/2009
JP   1-294532 A   11/1989
(Continued)

OTHER PUBLICATIONS

Chinese Office Action mailed Nov. 9, 2022 for the corresponding Chinese Patent Application No. 202080009669.0 (15 pages).
(Continued)

*Primary Examiner* — Smita S Patel
(74) *Attorney, Agent, or Firm* — Leason Ellis LLP; Edward J. Ellis; Melvin C. Garner

(57) ABSTRACT

Porous zirconia particles exhibit high specificity to a protein to be immobilized thereto and are used in immobilization of the protein. The porous zirconia particles have a pore diameter D50, at which a ratio of a cumulative pore volume to a total pore volume is 50%, the pore diameter D50 being in a range of 3.20 nm or more and 6.50 nm or less; and a pore
(Continued)

diameter D90, at which a ratio of a cumulative pore volume to a total pore volume is 90%, the pore diameter D90 being in a range of 10.50 nm or more and 100.00 nm or less. The total pore volume of the particles is greater than 0.10 cm$^3$/g. D50, D90, and the total pore volume are determined based on a pore diameter distribution measured through a BET method.

4 Claims, 3 Drawing Sheets

(51) Int. Cl.
    *B01J 20/28*     (2006.01)
    *C01G 25/02*     (2006.01)
    *B01J 20/30*     (2006.01)

(52) U.S. Cl.
    CPC ... *B01J 20/28069* (2013.01); *B01J 20/28078* (2013.01); *B01J 20/28088* (2013.01); *B01J 20/3042* (2013.01); *C01P 2006/14* (2013.01); *C01P 2006/17* (2013.01)

(58) Field of Classification Search
    CPC ............ B01J 20/28078; B01J 20/28088; B01J 20/3042; B01J 20/00; C01G 25/02
    See application file for complete search history.

(56) References Cited

U.S. PATENT DOCUMENTS

| 5,205,929 | A | 4/1993 | Carr et al. |
| 5,910,462 | A | 6/1999 | Gani et al. |
| 6,319,868 | B1 | 11/2001 | Gani et al. |
| 9,956,543 | B2 | 5/2018 | Kodama |
| 2016/0207027 | A1* | 7/2016 | Kodama .................. B01J 23/10 |

FOREIGN PATENT DOCUMENTS

| JP | 9-503989 A | 4/1997 |
| JP | 2015-189655 A | 11/2015 |
| JP | 2017-47365 A | 3/2017 |
| WO | WO-2007/021037 A1 | 2/2007 |

OTHER PUBLICATIONS

Subramanian et al. "Use of a modified zirconia support in the separation of immunoproteins", Journal of Chromatography A, 2002, pp. 179-187 (9pages).

Extended European Search Report mailed Oct. 20, 2022 for the corresponding European Patent Application No. 20745718.5 (6 pages).

International Search Report mailed Apr. 14, 2020 for the corresponding PCT International Application No. PCT/JP2020/001498.

* cited by examiner

POROUS ZIRCONIA PARTICLES, AND AGGREGATE FOR IMMOBILIZING PROTEIN

CROSS-REFERENCE TO RELATED PATENT APPLICATIONS

This application is a U.S. National Phase Application under 35 U.S.C. § 371 of International Patent Application No. PCT/JP2020/001498 filed on Jan. 17, 2020 and claims the benefit of priority to Japanese Patent Application No. 2019-010342 Jan. 24, 2019, the contents of both of which are incorporated herein by reference in their entireties. The International Application was published in Japanese on Jul. 30, 2020 as International Publication No. WO/2020/153253 under PCT Article 21(2).

FIELD OF THE INVENTION

The present invention relates to porous zirconia particles and to an aggregate for immobilizing protein.

BACKGROUND OF THE INVENTION

There have been investigated columns for separating and purifying a specific protein through selective adsorption of the specific protein.

For example, Japanese Patent Application Laid-Open (kokai) No. 2017-47365 discloses a technique for attaining the above object employing porous zirconia particles. According to this technique, protein A, serving as a ligand for achieving adsorption of protein, is bound to the surfaces of porous zirconia particles, to thereby enhance selectivity (specificity) to the protein of interest.

PRIOR ART DOCUMENTS

Patent Document 1: Japanese Patent Application Laid-Open (kokai) No. 2017-47365

Problems to be Solved by the Invention

However, the technique disclosed in Japanese Patent Application Laid-Open (kokai) No. 2017-47365 employs protein A, which problematically elevates the cost of the technique.

Under such circumstances, the present invention has been conceived, and thus an object of the invention is to provide inexpensive porous zirconia particles which exhibit high specificity to a protein to be immobilized thereto. The present invention can be implemented as the following modes.

SUMMARY OF THE INVENTION

Means for Solving the Problems

[1] Porous zirconia particles used for immobilization of a protein, characterized in that the particles have:
  a pore diameter D50, at which a ratio of a cumulative pore volume to a total pore volume is 50%, the pore diameter D50 being in a range of 3.20 nm or more and 6.50 nm or less;
  a pore diameter D90, at which a ratio of a cumulative pore volume to a total pore volume is 90%, the pore diameter D90 being in a range of 10.50 nm or more and 100.00 nm or less; wherein
  the total pore volume is greater than 0.10 cm$^3$/g, and D50, D90, and the total pore volume are determined based on a pore diameter (i.e., pore size) distribution measured through a BET method.
[2] The porous zirconia particles as described in [1], wherein the protein is immunoglobulin.
[3] The porous zirconia particles as described in [2], wherein the immunoglobulin is at least one species selected from the group consisting of IgG, IgE, and IgD.
[4] The porous zirconia particles as described in [1], wherein the porous zirconia particles have surfaces onto which a chelating agent is bound.
[5] An aggregate for immobilizing a protein, wherein the porous zirconia particles as described in [1] are aggregated.

Effects of the Invention

The porous zirconia particles of the present invention for use in immobilization of a protein, employing no protein as a ligand, are inexpensive. In addition, since the porous zirconia particles of the present invention have D50, D90, and a total pore volume falling within specific ranges, high selectivity (specificity) to a protein of interest can be attained.

When the protein to be immobilized is an immunoglobulin, the protein selectivity of the porous zirconia particles of the present invention is considerably high.

When the protein to be immobilized is at least one species selected from the group consisting of IgG, IgE, and IgD, the protein selectivity of the porous zirconia particles of the present invention is remarkably high.

When a chelating agent is bound to the surfaces of the porous zirconia particles of the present invention, the protein selectivity is further enhanced.

The aggregate for immobilizing a protein, which is formed through aggregating the porous zirconia particles of the present invention, is inexpensive and exhibits high protein selectivity.

DETAILED DESCRIPTION OF THE INVENTION

Figure 1:
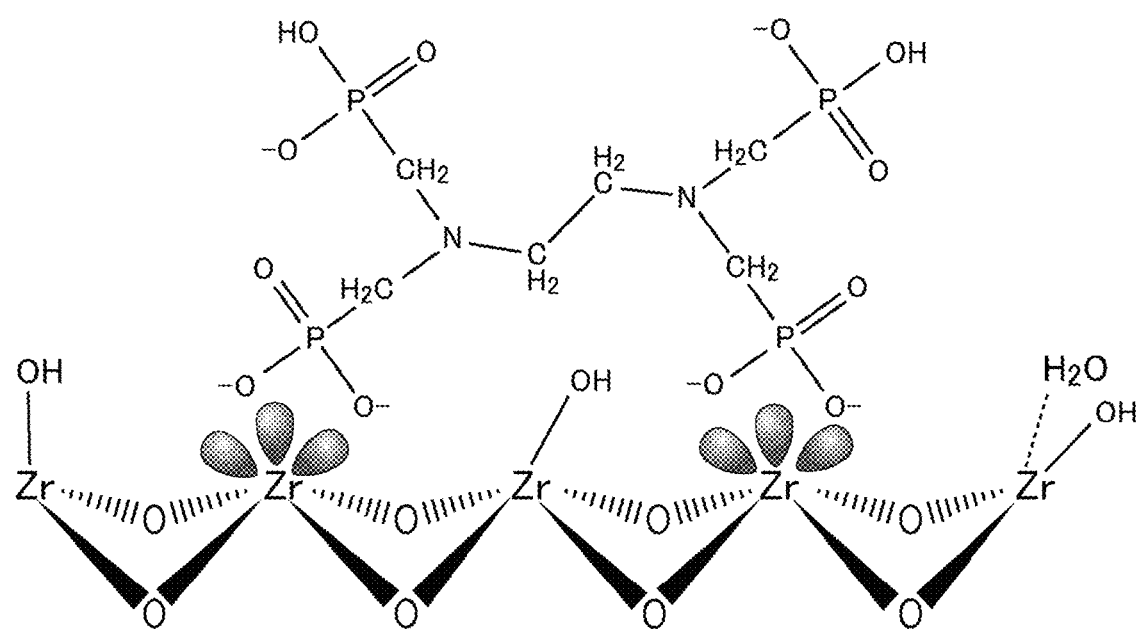
FIG. 1 is a schematic representation of a conceivable bonding feature of ethylenediaminetetramethylenephosphonic acid (EDTPA).

The present invention will next be described in detail. As used herein, unless otherwise specified, the numerical value range expressed by "(value) to (value)" includes the lower limit and the upper limit of the range. For example, the expression "10 to 20" includes both a lower limit of "10" and an upper limit of "20." That is, "10 to 20" is equivalent to "10 or more and 20 or less."

1. Porous Zirconia Particles

The porous zirconia particles of the present invention are used for immobilizing a protein (i.e., porous zirconia particles for use in immobilization of a protein).

(1) D50, D90, and Total Pore Volume

The porous zirconia particles have a pore diameter D50, at which a ratio of a cumulative pore volume to a total pore volume is 50%, of 3.20 nm or more and 6.50 nm or less, and a pore diameter D90, at which a ratio of a cumulative pore volume to a total pore volume is 90%, of 10.50 nm or more and 100.00 or nm or less, as determined in a pore diameter distribution measured through a BET method. The pore diameter D50 is preferably 3.35 nm or more and 6.30 nm or less, more preferably 3.50 nm or more and 5.00 nm or less. The pore diameter D90 is preferably 10.80 nm or more and 50.00 nm or less, more preferably 11.00 nm or more and 30.00 nm or less.

The total pore volume of the porous zirconia particles is greater than $0.10$ cm$^3$/g. The total pore volume is preferably greater than $0.15$ cm$^3$/g, more preferably greater than $0.30$ cm$^3$/g. No particular limitation is imposed on the upper limit of the total pore volume, and it is generally 10 cm$^3$/g.

When D50, D90, and the total pore volume satisfy the above conditions, the selectivity to a protein to be adsorbed is enhanced. Notably, through adjusting D90 to be 100.00 nm or less, selective immobilization of a monomeric protein is facilitated. A monomeric protein has a size of about 10 nm, while an aggregate of protein has a size of about 100 nm. Thus, D90 regulated to 100.00 nm or less avoids immobilization of an aggregate of protein and facilitates selective immobilization of a monomeric protein.

(2) Measurement Apparatus, and Method of Calculating D50 and D90

The pore diameter distribution and pore volume may be determined by means of, for example, a porosity analyzer (Micromeritics, automated surface area/porosity analyzer (TriStar II, product of Shimadzu Corporation)).

The calculation method will now be described.

Firstly, a method for calculating D50 is described. By use of data of a pore diameter distribution, two points A and B, which are respectively present above and below the line representing cumulative pore volume 50% and in the closest vicinity of the 50% line, are chosen. The cumulative pore volume (X (%)) and the pore diameter (Y(nm)) of each of the points A and B are read off. Specifically, point A (Xa (%), Ya (nm)) and point B (Xb (%), Yb (nm)) are read (wherein Xa>Xb, Ya>Yb). From these values, D50 is calculated by the following calculation formula (1):

$D50=\log(Xb)+((\log(Xa)-\log(Xb))*[(50-(Yb))/((Ya)-(Yb))]$      calculation formula (1).

In a similar manner, D90 is determined. Specifically, by use of the data of the pore diameter distribution, two points C and D, which are respectively present above and below the line representing cumulative pore volume 90% and in the closest vicinity of the 90% line, are chosen. The cumulative pore volume (X (%)) and the pore diameter (Y(nm)) of each of the points C and D are read off. More specifically, point C (Xc (%), Yc(nm)) and point D (Xd (%), Yd (nm)) are read (wherein Xc>Xd, Yc>Yd). From these values, D90 is calculated by the following calculation formula (2):

$D90=\log(Xd)+((\log(Xc)-\log(Xd))*[(90-(Yd))/((Yc)-(Yd))]$      calculation formula (2).

(3) Particle Diameter

No particular limitation is imposed on the particle diameter of the porous zirconia particles. However, the primary particles generally have a particle diameter of 10 nm to 100 nm, preferably 10 nm to 50 nm, more preferably 10 nm to 30 nm. When the primary particle diameter satisfies the above conditions, the specific surface area of the porous zirconia particles considerably increases, whereby the amount of immobilized protein tends to increase.

2. Protein

No particular limitation is imposed on the protein to be immobilized. The porous zirconia particles of the present invention are highly suitable for selectively immobilizing an immunoglobulin; in particular, at least one species selected from the group consisting of IgG, IgE, and IgD.

Notably, in the present invention, the concept "immobilization" encompasses both physical immobilization and chemical immobilization. The porous zirconia particles of the present invention immobilize protein in the pores thereof through physical immobilization (i.e., protein molecules are inserted into pores via capillarity) and on the zirconia surface through chemical immobilization employing a chemical bond (e.g., a covalent bond). Thus, the porous zirconia particles of the present invention exhibit high protein immobilization ability.

3. Chelating Agent

Onto the surfaces of the porous zirconia particles, a chelating agent may be bound. By virtue of the chelating agent supported on the zirconia particles, protein selectivity can be further enhanced.

No particular limitation is imposed on the chelating agent, and the chelating agent is preferably at least one species selected from the group consisting of a compound represented by the following formula (1), ethylenediaminetetraacetic acid (EDTA), diethylenetriaminepentaacetic acid (DETPA), diethylenetriaminepentamethylenephosphonic acid (DETPPA), and salts thereof. Examples of preferred salts include alkali metal (e.g., sodium) salts.

[F1]

$$PO_3H-R^2 \diagdown N-R^1-N \diagup R^4-PO_3H$$
$$PO_3H-R^3 \diagup \phantom{N-R^1-N} \diagdown R^5-PO_3H$$      (1)

(In formula (1), $R^1$ represents a C1 to C10 alkylene group. Each of $R^2$ to $R^5$, which may be identical to or different from one another, represents a C1 to C10 alkylene group.)

Examples of the C1 to C10 alkylene group of $R^1$ in formula (1) include methylene, ethylene, trimethylene, tetramethylene, hexamethylene, and isobutylene.

Examples of the C1 to C10 alkylene group of $R^2$ to $R^5$ include methylene, ethylene, trimethylene, tetramethylene, hexamethylene, and isobutylene.

From the viewpoint of enhancing selectivity to immunoglobulin, the chelating agent is preferably a compound represented by formula (1). Among compounds represented by formula (1), ethylenediaminetetramethylenephosphonic acid (i.e., N,N,N',N'-ethylenediaminetetrakis(methylenephosphonic acid)) (EDTPA) is particularly preferred.

No particular limitation is imposed on the amount of the bound chelating agent. From the viewpoint of enhancing selectivity to immunoglobulin, the amount of bound chelating agent is preferably 0.01 μg to 10 μg per 1 mg of zirconia, more preferably 0.02 μg to 5 μg, still more preferably 0.05 μg to 3 μg.

Notably, the amount of the bound chelating agent may be calculated by a reduction in weight as determined through TG-DTA (thermogravimetry-differential thermal analysis).

No precise bonding mode of the chelating agent has been elucidated. However, the mode is assumed such that a ligand derived from the chelating agent is bound to zirconium atoms. In the case where the chelating agent is ethylenediaminetetramethylenephosphonic acid, the bonding mode is assumed to be represented by the structure shown in FIG. 1.

4. Aggregate for Immobilizing Protein

The aggregate for immobilizing protein is formed through aggregation of porous zirconia particles. No particular limitation is imposed on the diameter (size) of the aggregate for immobilizing protein.

The diameter of the aggregate is generally 50 nm to 20,000 nm, preferably 100 nm to 15,000 nm, more preferably 500 nm to 10,000 nm. When the diameter of the aggregate satisfies the above conditions, separation through centrifugal sedimentation is easily carried out, whereby the total cost of the purification process can be reduced. Also, when the aggregate for immobilizing protein is used in a column, the aggregate may be granulated to a size of 20 μm to 100 μm.

5. Porous Zirconia Particle Production Method

No particular limitation is imposed on the method for producing the porous zirconia particles. The porous zirconia particles may be produced through, for example, the following procedure. Specifically, a zirconium oxychloride ($ZrOCl_2 \cdot 8H_2O$) solution is prepared from zircon as a raw material. Through hydrolysis of the solution, $Zr(OH)_4$ microparticles are formed. The microparticles are fired, to thereby yield porous zirconia particles.

Examples

The present invention will next be described in more detail by way of examples.

1. Experiment A (1) Porous Zirconia Particles

Porous zirconia particle products as listed in Table 1 were used.

Notably, Experimental Examples 1 to 9 correspond to examples, and Experimental Examples 10 to 17 correspond to comparative examples. In Table 1, each comparative example is denoted by the number of Experimental Example with the symbol "*" (e.g., 10*).

(2) Pore Diameter Distribution and Pore Volume

The pore diameter distribution and pore volume (total pore volume) were determined by means of Micromeritics, automated surface area/porosity analyzer (TriStar II, product of Shimadzu Corporation)). Each porous zirconia particle product was weighed in an amount of about 50 mg and dried at 80° C. for 3 hours under degassing, to thereby prepare a sample. The two values were calculated through BET method (nitrogen adsorption experiment).

D50 and D90 were calculated through the methods disclosed in "1. (1) D50, D90, and total pore volume" in the description of the specification.

(3) Immobilization of IgG and Determination of Amount of IgG

In the following manner, IgG was immobilized to each porous zirconia particle sample, and the amount of IgG immobilized to the sample was determined.

IgG was caused to be immobilized to porous zirconia particles through the following procedure. Firstly, 10 mM phosphate buffer (pH: 7.0) was placed in a Spitz tube (500 μL), and porous zirconia particles (3 mg) were added thereto. After completion of sufficient dispersion of the porous zirconia particles, IgG (500 μg/500 μL) (500 μL) was added to the dispersion, and the resultant mixture was stirred overnight at 4° C. under shielding from light.

The Spitz tube was subjected to centrifugation at 12,000 rpm for 10 minutes, to thereby precipitate the porous zirconia particles. The amount of free IgG remaining in the supernatant was quantitated by means of a microplate reader (Infinite F200PRO, product of TECAN) with a protein assay stain (product of BIO-RAD). The difference between the initial IgG amount and the amount of free IgG was employed as the amount of immobilized IgG.

(4) Results of Experiments

Figure 2:
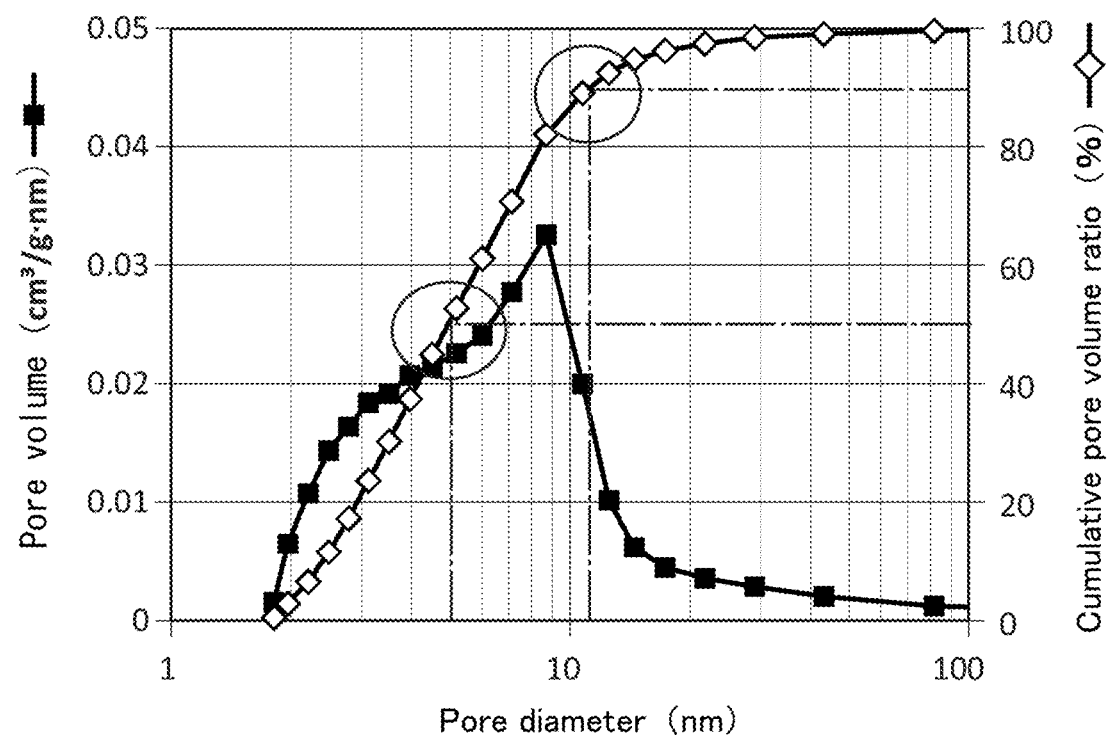
FIG. 2 is a graph showing a pore diameter distribution (pore distribution) of Experimental Example 3 (example).
Figure 3:
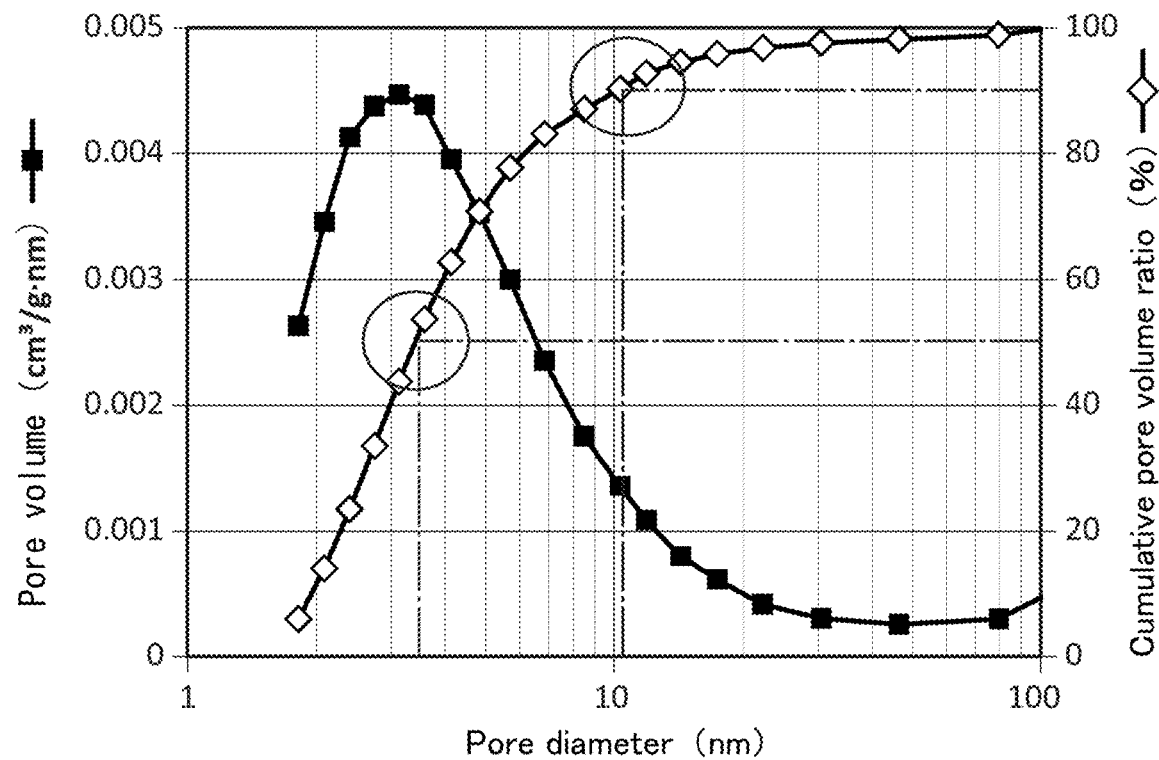
FIG. 3 is a graph showing a pore diameter distribution (pore distribution) of Experimental Example 13 (comparative example).

FIG. 2 shows a pore diameter distribution (pore distribution) of Experimental Example 3 (example), and FIG. 3

TABLE 1

| Experimental Ex. | Producer | Type | Immobilized IgG amount (μg) | D50 (nm) | D90 (nm) | Total pore vol. (cm3/g) |
|---|---|---|---|---|---|---|
| 1 | Nippon Denko | PCS 140 (SD) | 440.9 | 4.72 | 11.52 | 0.51 |
| 2 | Daiichi Kigenso | UEP100 | 438.4 | 4.82 | 15.14 | 0.51 |
| 3 | Nippon Denko | PCS 140 | 391.2 | 4.94 | 11.21 | 0.52 |
| 4 | Nippon Denko | PCS 90 | 380.9 | 6.27 | 13.95 | 0.47 |
| 5 | Nippon Denko | PCS 60 | 345.6 | 4.00 | 16.41 | 0.33 |
| 6 | Daiichi Kigenso | RC100 | 267.5 | 6.23 | 11.72 | 0.36 |
| 7 | Nippon Denko | PCS 30 | 256.0 | 3.37 | 11.37 | 0.21 |
| 8 | KCM | NF-S | 208.3 | 3.52 | 11.82 | 0.15 |
| 9 | Tosoh | TZ-3Y | 183.5 | 3.52 | 11.48 | 0.16 |
| 10* | KCM | CG | 88.2 | 3.41 | 9.74 | 0.08 |
| 11* | Marumi Toryo | PSZ-C1 | 54.6 | 3.37 | 10.10 | 0.09 |
| 12* | Daiichi Kigenso | DK-3CH | 52.9 | 3.33 | 9.51 | 0.08 |
| 13* | Zir Chrom | Rhinophase-AB | 40.3 | 3.41 | 10.18 | 0.07 |
| 14* | Aldrich | ZrO2 | 32.9 | 3.34 | 9.04 | 0.06 |
| 15* | Shin-Etsu Chem. | YSZ25 | 20.9 | 4.09 | 10.45 | 0.10 |
| 16* | Shin-Etsu Chem. | YSZ55 | 6.7 | 3.15 | 5.57 | 0.10 |
| 17* | Shin-Etsu Chem. | YSZ-QU | 3.5 | 3.45 | 9.19 | 0.05 |

In Table 1, "Nippon Denko" denotes "Nippon Denko Co., Ltd.," "Daiichi Kigenso" denotes "Daiichi Kigenso Kagaku Kogyo Co., Ltd.," "KCM" denotes "KCM Corporation," "Marumi Toryo" denotes "Marumi Toryo Kabushikigaisya," "Tosoh" denotes "Tosoh Corporation," "Zir Chrom" denotes "Zir Chrom Seperations Inc.," "Aldrich" denotes "Sigma-Aldrich Japan," and "Shin-Etsu Chem." denotes "Shin-Etsu Chemical Co., Ltd."

shows a pore diameter distribution (pore distribution) of Experimental Example 13 (comparative example). As is clear from FIG. 2, in Experimental Example 3, D50 was found to be 3.20 nm or more and 6.50 nm or less, and D90 was found to be 10.50 nm or more and 100.00 nm or less. Also, as is clear from FIG. 3, in Experimental Example 13, D50 was found to be 3.20 nm or more and 6.50 nm or less, and D90 was found to be less than 10.50 nm.

The results are also shown in Table 1. As is clear Table 1, Experimental Examples 1 to 9 (examples) satisfied the following requirements [1] to [3].

[1] A pore diameter D50 of 3.20 nm or more and 6.50 nm or less.
[2] A pore diameter D90 of 10.50 nm or more and 100.00 nm or less.
[3] A total pore volume greater than 0.10 cm$^3$/g.

In contrast, Experimental Examples 10 to 17 (comparative examples) failed to satisfy the following requirements.

Experimental Example 10 failing to satisfy requirements [2] and [3].
Experimental Example 11 failing to satisfy requirements [2] and [3].
Experimental Example 12 failing to satisfy requirements [2] and [3].
Experimental Example 13 failing to satisfy requirements [2] and [3].
Experimental Example 14 failing to satisfy requirements [2] and [3].
Experimental Example 15 failing to satisfy requirement [2].
Experimental Example 16 failing to satisfy requirements [1] and [2].
Experimental Example 17 failing to satisfy requirements [2] and [3].

Thus, as compared with Experimental Examples 10 to 17 (comparative examples), Experimental Examples 1 to 9 (examples) exhibited more excellent protein immobilizing ability.

2. Experiment B

In order to determine the maximum IgG immobilization amount, the procedure of Example A was repeated, except that IgG (750 μg/500 μL) for increasing the IgG supply was added in an amount of 500 μL. Thus, Experiment B was conducted. Other conditions employed in Experiment B were the same as those employed in Experiment A.

Table 2 shows the results.

(1) Porous Zirconia Particles

Porous zirconia particle products as listed in Table 3 were used.

In Table 3, "RC100" is a porous zirconia particle product of Daiichi Kigenso Kagaku Kogyo Co., Ltd., which was also used in Experimental Example 6 in Table 1. "UEP100" is a porous zirconia particle product of Daiichi Kigenso Kagaku Kogyo Co., Ltd., which was also used in Experimental Example 2 in Table 1.

In Table 3, "RC100-P (0.00125M)" is EDTPA-bound porous zirconia particles prepared by treating a porous zirconia particle product of Daiichi Kigenso Kagaku Kogyo Co., Ltd. (RC100, raw material) with 0.00125M EDTPA solution.

In Table 3, "UEP100-P (0.00125M)" is EDTPA-bound porous zirconia particles prepared by treating a porous zirconia particle product of Daiichi Kigenso Kagaku Kogyo Co., Ltd. (UEP100) with 0.00125M EDTPA solution.

Specifically, "RC100-P (0.00125M)" was prepared through the following procedure. Porous zirconia particles (RC100) were preliminarily dried at 100° C. for 2 hours under degassing. To the thus-dried product (250 mg), 0.00125M EDTPA solution (10 mL) was added, and the resultant mixture was degassed for 15 minutes and stirred and/or shaken for 17 hours, followed by further refluxing the mixture for 4 hours. The product was washed with pure water and freeze-dried, to thereby produce RC100-P (0.00125M).

"UEP100-P (0.00125M)" was prepared in the same manner as employed in the preparation of "RC100-P (0.00125M)." Specifically, the procedure of preparing "RC100-P (0.00125M)" was repeated, except that "UEP100" was used as a raw material instead of "RC100," to thereby prepare "UEP100-P (0.00125M)."

Also, the procedure of preparing RC100-P (0.00125M) was repeated, except that the concentration of the EDTPA solution was modified to 0.00125M, 0.0025M, 0.005M, and 0.01M, to thereby prepare four PCS140(SD)P (EDTA concentration) products.

TABLE 2

| Experimental Ex. | Producer | Type | Immobilized IgG amount (μg) | | D50 (nm) | D90 (nm) | Pore volume (cm3/g) |
|---|---|---|---|---|---|---|---|
| | | | IgG supply 500 μg | IgG supply 750 μg | | | |
| 1 | Nippon Denko | PCS 140 (SD) | 440.9 | 543.5 | 4.72 | 11.52 | 0.51 |
| 2 | Daiichi Kigenso | UEP100 | 438.4 | 629.9 | 4.82 | 15.14 | 0.51 |
| 4 | Nippon Denko | PCS 90 | 380.9 | 594.6 | 6.27 | 13.95 | 0.47 |
| 5 | Nippon Denko | PCS 60 | 345.6 | 515.2 | 4.00 | 16.41 | 0.33 |
| 7 | Nippon Denko | PCS 30 | 256.0 | 406.6 | 3.37 | 11.37 | 0.21 |
| 9 | Tosoh | TZ-3Y | 183.5 | 151.3 | 3.52 | 11.48 | 0.16 |

When porous zirconia particles having a total pore volume of 0.2 cm$^3$/g or more were used (Experimental Examples 1, 2, 4, 5, and 7), a greater amount of IgG was found to be immobilized at an amount of IgG used (IgG supply amount) of 750 μg than at an amount of IgG used (IgG supply amount) of 500 μg.

3. Experiment C

Next, there was investigated the effect, on protein selectivity, of binding ethylenediaminetetramethylenephosphonic acid (EDTPA) serving as a chelating agent onto porous zirconia particles.

Notably, the amount of bound EDTPA was calculated from a weight loss as determined through thermogravimetry-differential thermal analysis (TG-DTA). More specifically, EDTPA-bound porous zirconia particles (about 10 mg) were weighed, and the change in weight of the sample was measured in a temperature range of ambient temperature to 1,000° C. by means of a thermogravimetry-differential thermal analyzer (TG-DTA) (Thermo plus TG8120, product of Rigaku). From the weight loss in the range of 200° C. to 600° C., the porous zirconia particles were found to have EDTPA bound onto the surfaces thereof in an amount of 0.06 μg to 2.2 μg per 1 mg of the particles.

TABLE 3

| | Porous zirconia particles | | | | | | | | | | | |
|---|---|---|---|---|---|---|---|---|---|---|---|---|
| | RC100 | | | RC100-P(0.00125M) | | | UEP100 | | | UEP100-P(0.00125M) | | |
| Protein type | IgG | HAS | Trf | IgG | HAS | Trf | IgG | HAS | Trf | IgG | HAS | Trf |
| Amount of immobilized protein (μg/3 mg) | 267.5 | 22.5 | 17.9 | 274.2 | 0.0 | 0.0 | 438.4 | 64.3 | 28.5 | 418.4 | 4.1 | 0.0 |

(2) Protein Selectivity Test

Selectivity to protein was determined by use of porous zirconia particles (RC100, UEP100) and EDTPA-bound porous zirconia particles (RC100-P, UEP100-P).

More specifically, protein selectivity of the above 4 porous zirconia particles was determined with respect to 3 proteins; IgG, HAS (albumin from human serum), and Trf (transferrin human). The specific test procedure is as follows.

Firstly, 10 mM phosphate buffer (pH: 7.0) was placed in a Spitz tube (500 μL), and porous zirconia particles (3 mg) were added thereto. After completion of sufficient dispersion of the porous zirconia particles, a protein (500 μg/500 μL) (500 μL) was added to the dispersion, and the resultant mixture was stirred overnight at 4° C. under shielding from light.

The Spitz tube was subjected to centrifugation at 14,000 rpm for 5 minutes, to thereby precipitate the porous zirconia particles. The amount of free protein remaining in the supernatant was quantitated by means of a microplate reader (Infinite F200PRO, product of TECAN) with a protein assay stain (product of BIO-RAD). The difference between the initial protein amount and the amount of free protein was employed as the amount of immobilized protein.

(3) Results of Experiments

Table 3 shows the results.

At first, test results of porous zirconia particles RC100 and EDTPA-bound porous zirconia particles RC100-P are assessed.

To porous zirconia particles RC100, HAS and Trf were found to be immobilized in addition to IgG.

To EDTPA-bound porous zirconia particles RC100-P, IgG was immobilized, but HAS and Trf were found to be not immobilized.

The test results have proven that the selective specificity to IgG can be enhanced by use of EDTPA-bound porous zirconia particles RC100-P, prepared by binding EDTPA onto porous zirconia particles RC100.

Next, test results of porous zirconia particles UEP100 and EDTPA-bound porous zirconia particles UEP100-P are assessed.

To porous zirconia particles UEP100, HAS and Trf were found to be immobilized in addition to IgG. The amount of immobilized HAS was 64.3 μg, and the amount of immobilized bound Trf was 28.5 μg.

To EDTPA-bound porous zirconia particles UEP100-P, HAS was found to be immobilized in addition to IgG, but the amount of immobilized HAS was 4.1 μg, which was considerably smaller than 64.3 μg achieved in the case of porous zirconia particles UEP100. Also, Trf was found to be not immobilized to EDTPA-bound porous zirconia particles UEP100-P.

The results have proven that the selective specificity to IgG can be enhanced by use of EDTPA-bound porous zirconia particles UEP100-P, prepared by binding EDTPA onto porous zirconia particles UEP100.

4. Effects Proven in Examples

When D50, D90, and the total pore volume fall within specific ranges, the porous zirconia particles can selectively immobilize IgG, which is an example of protein.

When EDTPA, which is an example of a chelating agent, is bound to the surfaces of porous zirconia particles, protein selectivity can be further enhanced.

Other Embodiments (Variations)

The invention is not limited to the aforementioned Examples and embodiments and may be carried out in various modes, so long as they do not deviate the scope of the invention.

INDUSTRIAL APPLICABILITY

By virtue of a zirconia crystal phase, the porous zirconia particles of the present invention exert advantageous effects which were not attained through conventional techniques; e.g., chemical resistance, high structural strength, and reusability by firing, when the porous zirconia particles are used in separation and purification of an antibody. Thus, the porous zirconia particles of the present invention are expected to greatly reduce cost for a process for producing antibody products. The porous zirconia particles of the present invention find use in column materials for the separation and purification of antibodies including antibody drugs, and also removal of a specific protein such as an allergen in food.

The invention claimed is:

1. Porous zirconia particles for immobilization of a protein, characterized in that the porous zirconia particles have:
   a pore diameter D50, at which a ratio of a cumulative pore volume to a total pore volume is 50%, is in a range of 3.20 nm or more and 6.50 nm or less; and
   a pore diameter D90, at which a ratio of a cumulative pore volume to the total pore volume is 90%, is in a range of 10.50 nm or more and 100.00 nm or less, wherein the total pore volume is greater than 0.10 cm$^3$/g, and
   wherein the pore diameter D50, the pore diameter D90, and the total pore volume are determined based on a pore diameter distribution measured through a BET method.

2. The porous zirconia particles according to claim 1, wherein the protein is immunoglobulin.

3. The porous zirconia particles according to claim 2, wherein the immunoglobulin is at least one species selected from the group consisting of IgG, IgE, and IgD.

4. The porous zirconia particles according to claim 1, wherein the porous zirconia particles have surfaces onto which a chelating agent is bound.

* * * * *